(12) United States Patent
Kjeldsen et al.

(10) Patent No.: US 9,604,007 B2
(45) Date of Patent: Mar. 28, 2017

(54) MEDICAL INJECTION SYSTEM COMPRISING A MEDICAL INJECTION DEVICE AND A DOSE LIMITER MODULE

(71) Applicant: Novo Nordisk A/S, Bagsvaerd (DK)

(72) Inventors: Bastian Gaardsvig Kjeldsen, Hilleroed (DK); Brian Mouridsen, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/355,460

(22) PCT Filed: Nov. 8, 2012

(86) PCT No.: PCT/EP2012/072168
§ 371 (c)(1),
(2) Date: Apr. 30, 2014

(87) PCT Pub. No.: WO2013/068483
PCT Pub. Date: May 16, 2013

(65) Prior Publication Data
US 2014/0257195 A1 Sep. 11, 2014

Related U.S. Application Data

(60) Provisional application No. 61/558,206, filed on Nov. 10, 2011.

(30) Foreign Application Priority Data

Nov. 8, 2011 (EP) ..................... 11188149

(51) Int. Cl.
*A61M 5/315* (2006.01)
(52) U.S. Cl.
CPC ...... *A61M 5/31541* (2013.01); *A61M 5/3155* (2013.01); *A61M 5/31553* (2013.01); *A61M 2005/3154* (2013.01)

(58) Field of Classification Search
CPC .. A61M 2005/3131; A61M 2005/3137; A61M 2005/3139; A61M 2005/3142;
(Continued)

(56) References Cited

U.S. PATENT DOCUMENTS

| 4,592,745 A | 6/1986 | Rex et al. |
|---|---|---|
| 5,308,340 A | 5/1994 | Harris |

(Continued)

FOREIGN PATENT DOCUMENTS

| CN | 101068586 A | 11/2007 |
|---|---|---|
| CN | 201375731 Y | 1/2010 |

(Continued)

*Primary Examiner* — Bhisma Mehta
*Assistant Examiner* — Hamza Darb
(74) *Attorney, Agent, or Firm* — Wesley Nicolas

(57) ABSTRACT

The present invention relates to a medical injection system comprising a medical injection device (100) of the type comprising a rotatable dose setting member (160). The system further comprises a dose limiter module (200) adapted for being releasably coupled to the injection device (100). The dose limiter module (200) comprises a dose limiter base (201) and a limiter (240) arranged relative to the dose limiter base (201) so that their relative position is adjustable to set an adjusted dose limiting position. When the dose limiter module (200) is coupled to the injection device (100), the limiter (240) cooperates with the dose setting member (160) to define a blocking means for preventing rotation of the dose setting member (160) beyond the adjusted dose limiting position. The dose limiter module (200) further comprises a user operable lock (210,212,232, 223,243) configured for operation between a locked state and an unlocked state to respectively prevent and enable modification of the adjusted dose limiting position, the lock (210,212,232,223,243) being configured for maintaining the (Continued)

lock in the locked state at least when the dose limiter module (200) is not coupled with the injection device (100).

15 Claims, 4 Drawing Sheets

(58) Field of Classification Search
CPC .............. A61M 5/344; A61M 5/31541; A61M 5/31553; A61M 5/3155; A61M 2005/3154; A61M 5/31593; A61M 5/31548; A61M 5/31533; A61M 5/31558; A61M 5/31525; A61M 5/31561; A61M 5/3298; A61M 5/3129
USPC .................................................. 604/207–212
See application file for complete search history.

(56) References Cited

U.S. PATENT DOCUMENTS

| | | |
|---|---|---|
| 5,514,097 A | 5/1996 | Knauer |
| 6,752,787 B1 | 6/2004 | Causey, III et al. |
| 7,377,913 B2 | 5/2008 | Gurtner |
| 8,444,606 B2 | 5/2013 | Radmer et al. |
| 2009/0069742 A1 | 3/2009 | Larsen |
| 2009/0275916 A1 | 11/2009 | Harms et al. |
| 2010/0324527 A1 | 12/2010 | Plumptre |
| 2013/0253440 A1* | 9/2013 | Smith ............... A61M 5/31565 604/246 |

FOREIGN PATENT DOCUMENTS

| | | |
|---|---|---|
| CN | 101829381 | 9/2010 |
| EP | 1559443 A1 | 8/2005 |
| JP | 2008-521534 A | 6/2008 |
| WO | 01/54757 A1 | 8/2001 |
| WO | 01/91833 A1 | 12/2001 |
| WO | 2006/089767 A1 | 8/2006 |
| WO | 2010/098928 A1 | 9/2010 |
| WO | 2010/139638 A1 | 12/2010 |
| WO | 2010149209 A1 | 12/2010 |
| WO | 2011073302 A1 | 6/2011 |
| WO | 2012/072569 A1 | 6/2012 |

\* cited by examiner

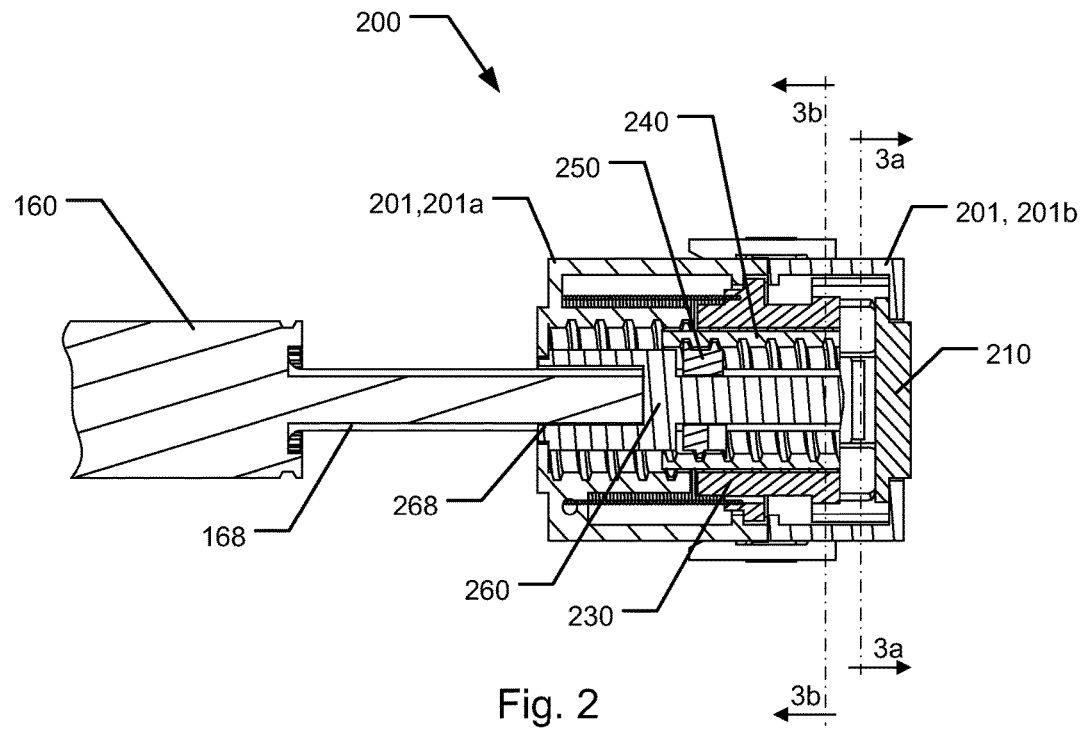
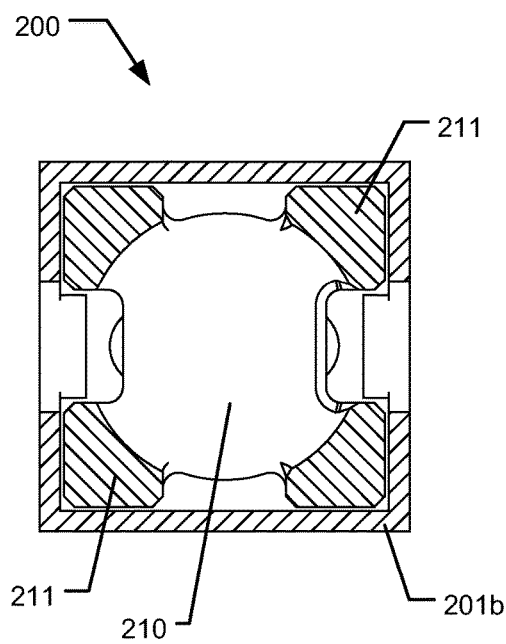
Fig. 3a
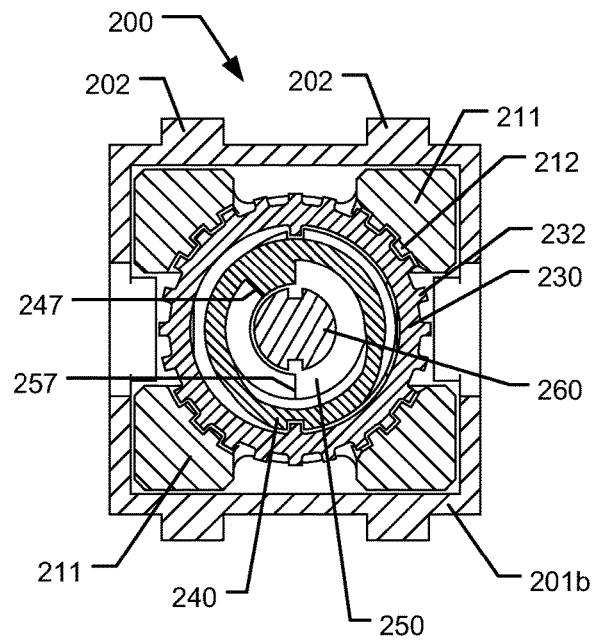
Fig. 3b

MEDICAL INJECTION SYSTEM COMPRISING A MEDICAL INJECTION DEVICE AND A DOSE LIMITER MODULE

CROSS-REFERENCE TO RELATED APPLICATIONS

This application is a 35 U.S.C. §371 National Stage application of International Application PCT/EP2012/072168 (published as WO 2013/068483), filed Nov. 8, 2012, which claimed priority of European Patent Application 11188149.6, filed Nov. 8, 2011; this application claims priority under 35 U.S.C. §119 of U.S. Provisional Application 61/558,206; filed Nov. 10, 2011.

The present invention generally relates to medical injection systems and to medical injection devices adapted for managing medical therapy as well as components for use in such devices. More specifically, the invention relates to medical delivery devices for setting and injecting set doses of a medicament and measures for facilitating safe and user-friendly dose setting.

BACKGROUND OF THE INVENTION

In the disclosure of the present invention reference is mostly made to the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be highly sophisticated electronically controlled instruments with numerous functions. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. While pen-style injection devices are typically cylindrically shaped with a needle protruding from the most distal portion of one end of the device, some devices have other shapes with the needle no longer protruding from the most distal part of an end of the device, e.g. Innovo® and InnoLet® from Novo Nordisk A/S, Bagsvaerd, Denmark.

Typically, injection devices use a pre-filled cartridge containing the medication of interest, e.g. 1.5 or 3.0 ml of insulin or growth hormone. The cartridge is typically in the form of a generally cylindrical transparent ampoule with a needle pierceable septum at one end and an opposed piston designed to be moved by the dosing mechanism of the injection device. The injection devices generally are of two types: "Durable" devices and "disposable" devices. A durable device is designed to allow a user to replace one cartridge with another cartridge, typically a new cartridge in place of an empty cartridge. In contrast, a disposable device is provided with an integrated cartridge which cannot be replaced by the user; when the cartridge is empty the entire device is discarded.

Typical injection devices available today incorporates a dose setting feature where selection among a large variety of dose sizes may be performed by rotating a dose setting member. Although the dose selection thus provides for great flexibility and therefore being suitable for patients having different needs, the large variety in selecting the proper size of a dose may for some patients appear unnecessary complicated. This is especially the case for patients which are on a fixed dose regime. Also, from a safety point of view, the possibility of selecting a larger dose than intended may present a safety issue if a patient, such as a child performing a self-injection, by mistake adjusts the dose setting member for such an excessively large dose.

A series of recent publications relate to additional provisions for inclusion in manually injectors where an adjustable dose limiting element is incorporated to render the maximally selectable dose size adjustable, either by the individual patient or by the care-giver. Such dose limiting feature may be formed integral with the injection device as disclosed in U.S. Pat. No. 5,308,340, U.S. Pat. No. 5,514,097, US 2010/0324527 and in WO 2006/089767 A1.

Also, in particular for disposable devices, such dose limiting feature may be formed as an add-on which couples to the disposable device to limit the maximally selectable dose size. Examples of such devices are disclosed in U.S. Pat. No. 7,377,913 B2 and in WO 01/54757 A1.

While both the latter references provides the user with the possibility to limit the maximum selectable dose size from a disposable device by means of an add-on device, the maximum dose limit needs to be adjusted each time a new disposable injection device is to be put into use. Hence, such solutions require particular care each time the add-on device is mounted on the disposable device and there is a risk that the add-on will be not be used by the patient. A further limitation of those add-on devices is that they are limited for use with injection devices where the range of settable doses is limited to rotation within a single rotation.

Having regard to the above, it is an object of the present invention to provide a dose limiter module which enables a more user friendly operation of an associated medical injection device and which offers improvements in safety as compared with medical injection devices of the prior art.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a dose limiter module for cooperation with an injection device is provided, the injection device being of the type configured for setting and injecting set doses of a drug from a reservoir and comprising a) a housing and b) a rotatable dose setting member, and wherein the injection device is configured so that: i) during dose setting, the dose setting member is rotated in a first rotational direction from a first rotational position to a second rotational position in accordance with the size of a dose to be injected, and ii) during dose injection, the dose setting member is rotated counter to said first rotational direction back to said first rotational position. The dose limiter module is adapted for being releasably coupled to the injection device to define a coupled state where the dose limiter module is attached to the injection device and to define a decoupled state where the dose limiter module is detached from the injection device. The dose limiter module comprises a dose limiter base and a limiter arranged relative to the dose limiter base so that the relative position between the limiter and the dose limiter base is adjustable to set an adjusted dose limiting position. In the coupled state, the limiter cooperates with the dose setting member to define a blocking means for preventing rotation of the dose setting member beyond the adjusted dose limiting position when the dose setting member is rotated in the first rotational direction. The dose limiter module further comprises a user operable lock configured for operation between a locked state and an unlocked state to respectively prevent and enable adjustment of the position of the limiter relative to the dose limiter base, the lock being configured for maintaining the lock in the locked state at least when the dose limiter module is in the decoupled state.

Hence, in accordance herewith a dose limiter module is provided which retains the settings of an adjusted maximum dose limitation even when the module is detached from a first injection device and also after mounting the module onto a new device.

In one form of dose limiter module the lock is configured so that, when the dose limiter module is in the coupled state, the lock is shiftable into its unlocked state to enable adjustment of the position of the limiter relative to the dose limiter base. Hence, compared to the dose limiting solutions of the prior art, an easier setting procedure is enabled.

The lock of the dose limiter module may comprise a lock operating means that upon user operation shifts the lock from the locked state to the unlocked state to enable movement of the limiter relative to dose limiter base. Some embodiments may be configured for coupling the dose limiter module in a first state or position to the injection device wherein adjustment of the position of the limiter relative to the dose limiter base is enabled and wherein the dose limiter module may be moved for being coupled with the injection device in a second state or position wherein the lock is shifted into its locked state. Alternatively, the lock operation means may be provided as a user operable button which upon activation releases the lock. A biasing element may be configured for acting to maintain the lock in the locked state. Alternatively, or in addition, a snap mechanism is configured for releasably maintaining the lock in the locked state.

The lock of the dose limiter module may include a lock mechanism that prevents inadvertent movement of the limiter relative to the limiter base and may comprise a toothed engagement between members of the lock mechanism where the toothed engagement is released when the lock shifts from the locked state to the unlocked state. In other forms the lock mechanism may comprise a friction based engagement between members of the lock mechanism where the frictional engagement is released when the lock shifts from the locked state to the unlocked state.

According to some embodiments, the limiter may comprise a first thread that engages a thread associated or defined by the dose limiter base. In such embodiments, the position of the limiter relative to the dose limiter base is adjusted by relative rotation between the limiter and the dose limiter base. The limiter may be configured rotatably arranged relative to the dose limiter base to be adjustable through a relative movement exceeding 360 degrees. The total amount of the rotational movement of the limiter relative to the dose limiter base may in some embodiments correspond to the amount of full and incremental rotations that the dose setting member of the injection device experiences as it is dialed from a zero position into a maximum dose position, the maximum dose position being determined by the dose setting mechanism of the injection device when no dose limiter module is coupled to the injection device.

The dose limiter module may be so configured that when the dose limiter module is in the coupled state, the position of the limiter relative to the dose limiter base is adjustable by means of the dose setting member of the injection device.

In some embodiments, the dose limiter module includes a visible indicator that indicates the particular setting that corresponds to the setting of the adjusted dose limiting position. Such visible indicator may be provided as a series of dose indications where only the particular dose indication that corresponds to the adjusted dose limiting position is viewable. In some forms, the visible indicator is viewable through a window provided at an exterior surface of the module. In other forms, the visible indicator is only viewable when the dose limiter module is in its decoupled state.

The limiter and the dose limiter base may also be so configured that the limiter is movable between a minimum dose limiting position and a maximum dose limiting position and wherein the dose limiter module further comprises a spring adapted to act upon the limiter for urging the limiter towards its minimum dose limiting position so that when the limiter is positioned away from the minimum dose limiting position the limiter moves automatically towards the minimum dose limiting position when the lock is shifted into its unlocked state.

The dose limiter module may in some embodiments comprise a cam and cam follower mechanism where the cam follower is moved along the cam from a first position into an adjustable dose limiting position and wherein the cam follower is moved as the dose setting member of the injection device is dialed up and down and when the dose is injected. When the cam follower assumes the adjusted dose limiting position, the blocking means serves to prevent the dose setting member to be further dialed up.

In other embodiments of a dose limiter module, when the dose limiter module is in the coupled state, the module and the injection device defines:
    a first member that, at least in the locked state, is non-rotatably mounted relative to the dose limiter base, the first member defining a generally cylindrical surface defining first track surface selected as one of a thread or a longitudinal track,
    a second member that rotates around a central axis and that follows rotation of the dose setting member, the second member defining a generally cylindrical surface defining a second track surface selected as one of a thread or a longitudinal track, and
    a track follower arranged between the first member and the second member, the track follower defining a first geometry for engaging the first track surface of the first member and a second geometry for engaging the second track surface of the second member. In such dose limiter module, the first track surface is defined as one of a thread or a longitudinal track for engagement with the first geometry of the track follower while the second track surface is defined as the other one of a thread or a longitudinal track for engagement with the second geometry of the track follower. In such configuration, the track follower and the surface of the first or second member that defines the thread is being forced to rotate relative to each other and the track follower is caused to move along the central axis when the dose setting member is rotated. The limiter then forms part of said blocking means for blocking rotation of the dose setting member in the first rotational direction by blocking axial and/or rotational movement of the track follower in accordance with the adjusted position of the limiter relative to the dose limiter base.

In still other embodiments of a dose limiter module, when the dose limiter module is in the coupled state, the module and the injection device defines:

a first member that, at least in the locked state, is non-rotatably mounted relative to the dose limiter base, the first member defining a cylindrical surface defining a first thread, a second member that rotates around a central axis and that follows rotation of the dose setting member, the second member defining a cylindrical surface having a second thread, and a track follower arranged between the first member and the second member, the track follower defining a first geometry for engaging the first thread of the first member and a second geometry for engaging the second thread of the second member. In such dose limiter module, the pitch of the first thread is different to the pitch of the second thread so that the track follower rotates around the central axis and moves along the central axis when the dose setting member is rotated. The limiter forms part of said blocking means for blocking rotation of the dose setting member in the first rotational direction by blocking axial movement of the track follower in accordance with the adjusted dose limiting position of the limiter relative to the dose limiter base.

The term "pitch" according to instant invention shall preferably mean the distance between consecutive contours on a helical thread, measured parallel to the axis of the helical thread.

The blocking means for blocking rotation of the dose setting member in the first rotational direction by blocking axial movement of the track follower may both be provided as an axial blocking engagement between the track follower and the limiter or by providing a rotational blocking between respective rotational blocking surfaces defined by the track follower and by the limiter.

In accordance with the above embodiments including said first and second members, the limiter may in some embodiments define said first member. In other embodiments, the first member may be a component separate from the limiter.

In embodiments of the dose limiter module where it incorporates a spring adapted to act upon the limiter for urging the limiter towards its minimum dose limiting position, the limiter moves automatically into abutment with the track follower when the lock is shifted to the unlocked state.

The dose limiter module may be provided in forms where the dose limiter module defines both the track follower and the second member so that when the dose limiter module is in the decoupled state, i.e. separated from the injection device, the track follower and the second member forms part of the dose limiter module. In other embodiments, either the second member or both the second member and the track follower is incorporated in the housing of the injection device when the injection device and the dose limiter module is in the decoupled state, whereby the track follower of the device is adapted to engage the first member of the dose limiter module when the injection device and the dose limiter module is in the coupled state.

In other embodiments of a dose limiter module, the module is adapted to cooperate with an injection device that includes a rotational dose element that defines a helical thread engaging a helical thread associated with the housing of the injection device. Said rotational dose element may be adapted to rotate with the dose setting member. The limiter of the dose limiter module may then be adapted to engage the rotational dose element for preventing rotation of the dose setting member beyond the adjusted dose limiting position when the dose setting member is rotated in the first rotational direction. In such injection device, a dose dial scale may define said rotational dose indicating element.

In a dose limiter module in the above described simple embodiment, the rotational dose element may define one or more rotational blocking surfaces and the limiter may define corresponding one or more rotational counter blocking surfaces. The one or more rotational blocking surfaces engage respective ones of the one or more counter blocking surfaces for preventing rotation of the dose setting member beyond the adjusted dose limiting position when the dose setting member is rotated in the first rotational direction.

The reservoir of the medical injection device may in some embodiments be provided in the form of a cylindrical cartridge having a pierceable septum which covers an outlet portion of the cartridge and a slideable piston arranged to be moved towards the outlet for expelling the drug accommodated in the cartridge. In other embodiments, the reservoir forms a collapsible reservoir with an outlet and where a collapsible portion collapses as drug is expelled from the reservoir.

In some embodiments, the outlet portion of the reservoir may be configured to cooperate with an injection needle, such as a double-pointed injection needle.

The injection device may define an activation device, which when being activated causes a set dose of a drug to be expelled from the injection device.

The injection device defines a drive mechanism that is configured to expel set doses of a drug contained in the reservoir. The drive mechanism may be so configured that when the activation device is in its activated state the rotation of the dose setting member occurs in synchronism with a drive movement of a component that expels the set dose from the reservoir. Where the reservoir is a piston equipped cartridge, the drive mechanism may include a piston rod adapted to drive forward the piston. In some embodiments, the piston rod drives forward the piston when the dose setting member is rotated counter to said first rotational direction but exclusively when the activation device is in its activated state.

The injection device may form a manual injector where the user directly delivers the necessary mechanical energy during the expelling process. In other embodiments, the injection device forms a spring assisted injector where a pre-stressed or user strained spring partly or fully delivers the necessary mechanical energy during the expelling process.

In some embodiments the activation device forms an injection button. In other embodiments the activation device forms a member or assembly that is adapted to abut a skin portion at an injection site of the user so that when the housing of the injection device is pressed against the injection site, the activation device is moved relative to the housing of the injection device causing the injection movement to be initiated.

In accordance with the above embodiments, the housing of the injection device may be so shaped and sized as to allow it to be held in a hand and to be easily carried in a pocket. In some embodiments, the housing is formed to define a so-called doser form factor. In such device, the dose setting member may be configured for rotation around a first axis where the dose injection mechanism is adapted to move forward a piston of the reservoir along a second axis parallel with but separated from the first axis. The dose limiter module may be arranged to couple with the injection device generally along the first axis for coupling a limiter and/or a track follower to the dose setting member and so as to be movable along the first axis. In some embodiments the dose limiter module is connectable to the injection device at the distal end of the device. In other embodiments, the dose limiter module is connectable to the injection device at the proximal end of the device.

In accordance with a second aspect of the invention a dose limiter module for cooperation with an injection device is provided, the injection device being of the type configured for setting and injecting set doses of a drug from a reservoir and comprising a) a housing and b) a rotatable dose setting member, and wherein the injection device is configured so that: i) during dose setting, the dose setting member is rotated in a first rotational direction from a first rotational position to a second rotational position in accordance with the size of a dose to be injected, and ii) during dose injection, the dose setting member is rotated counter to said first rotational direction back to said first rotational position. The dose limiter module is adapted for being releasably coupled to the injection device to define a coupled state where the dose limiter module is attached to the injection device and to define a decoupled state where the dose limiter module is detached from the injection device. The dose limiter module comprises a dose limiter base and a limiter. Associated with the dose limiter base is a thread and the limiter has a thread engaged with the thread associated with the dose limiter base. The limiter and the dose limiter base are adapted for relative rotation over an angle exceeding 360 degrees in order to adjust the dose limiter module to define an adjusted dose limiting position. In the coupled state, the limiter cooperates with the dose setting member to define a blocking means for preventing rotation of the dose setting member beyond the adjusted dose limiting position when the dose setting member is rotated in the first rotational direction.

In some embodiments the thread associated with the dose limiter base is a thread formed by the dose limiter base. In other embodiments, the thread associated with the dose limiter base is a component that is made separate from the dose limiter base.

Any of the features mentioned above in relation to the first aspect of the invention and which logically combines with the features of the second aspect of the invention may be used to define subject matter providing further beneficial embodiments of the invention.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. Representative drugs include pharmaceuticals such as peptides (e.g. insulins, insulin containing drugs, GLP-1 containing drugs as well as derivates thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs. Correspondingly, the term "subcutaneous" delivery is meant to encompass any method of transcutaneous delivery to a subject.

BRIEF DESCRIPTION OF THE DRAWINGS

In the following the invention will be further described with references to the drawings, wherein:

FIG. 2 shows a cross sectional side view of a first embodiment of a dose limiter module cooperating with a dose setting member of an associated injection device, FIG. 3a shows a cross sectional end view of the dose limiter module along lines 3a-3a, FIG. 3b shows a cross sectional view of the dose limiter module along lines 3b-3b.

DESCRIPTION OF EXEMPLARY EMBODIMENTS

Figure 1:
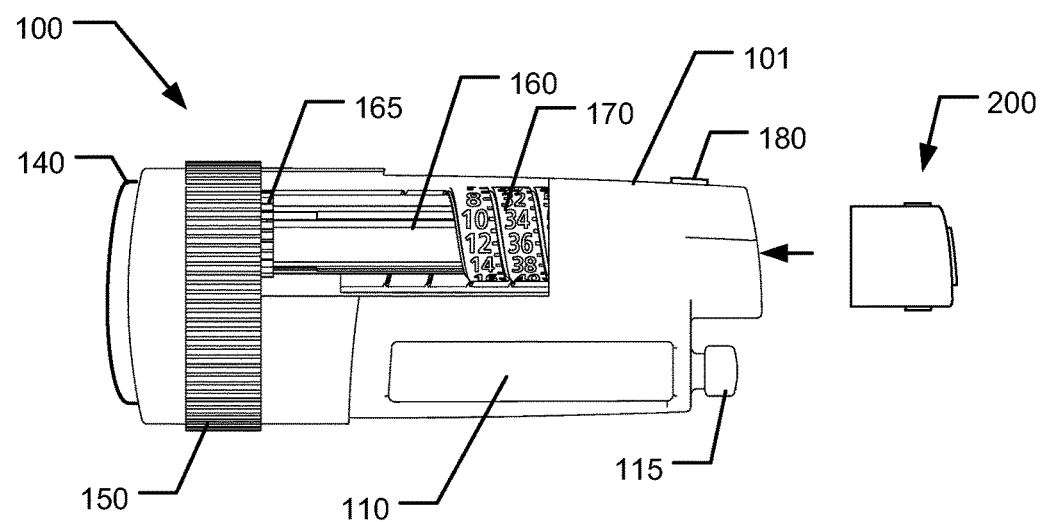
FIG. 1 shows a schematic representation of an injection device for setting and injecting set doses and a dose limiter module adapted to be coupled with the injection device.

FIG. 1 shows a schematic side view representation of an embodiment of a medical injection system incorporating an injection device 100 for use by a patient for setting one or more doses of a medicament for subsequent injection, the device 100 being adapted to receive and couple with a replaceable dose limiter module 200 according to the invention. In the drawing injection device 100 is shown as the type of device which generally in the art is referred to as a "doser" device having a housing 101 that is relatively short and flat as compared with injection devices of the so-called pen-shaped form factor. The device 100 is shown as a cartridge-based device incorporating a drug reservoir in the form of a piston equipped cartridge 110 having a pierceable septum which covers an outlet portion 115 of the cartridge 110. The pierceable septum is intended for cooperation with a replaceable subcutaneous needle (not shown) allowing a user to mount a fresh and sterile needle before each subcutaneous injection. At the initial stage of use, the piston of the cartridge 110 will typically be arranged at a proximal end of cartridge 110. The piston is slideably arranged in cartridge 110. In order to expel the drug contained in cartridge 110 out through the attached needle it may be forced towards the distal end, i.e. towards the outlet portion 115. The injection device may further include a cap (not shown) which detachably mounts relative to the distal end of housing 101 for protection of the contents of the cartridge 110 and eventually for protecting an injection needle which may be mounted at the distal end of the device.

The injection device 100 includes a housing 101 having proximal and distal ends. In FIG. 1, for the purpose of clarifying the working principle of the present invention the housing 101 is shown with cut-away portions which reveal elements of the injection device 100 of particular relevance for the dose setting and limiting function. The housing 101 accommodates cartridge 110 and accommodates a drive mechanism configured to drive the piston of the cartridge 110 during an expelling operation. The drive mechanism furthermore provides for setting a dosage amount which will be expelled upon subsequent activation of an activation device in the form of an injection button 140, the injection button 140 being arranged at the proximal end of housing 101.

An operable control member in the form of a flexible band 150 encircles a section of the housing 101 at the proximal end of housing 101. In the shown embodiment the flexible band 150 forms an endless loop. The flexible band 150 is adapted to slide relative to the housing 101 along the extension of the flexible band 150. In the shown embodiment, during a dose setting process, the flexible band 150 may be manually gripped and turned in one direction relative to housing 101 away from an initial position (the zero position) in order to dial up the set dose amount. In order to dial down an initially set dose the flexible band 150 may be turned in the opposite direction back towards the zero position.

Housing 101 further includes a window or opening (not shown) which provides visual inspection to a mechanically based dose dial scale 170 arranged internally in housing 101. Dose dial scale 170 includes various printed indicia, such as numerals, printed thereon, each indicia corresponding to the respective dose sizes that the dose setting part of drive mechanism is designed to assume. The dose dial scale 170 is operated by means of flexible band 150 as it is turned relative to the housing 101 during the dose setting process.

In embodiments where the injection device is adapted for injecting insulin-type medicaments, the dose size may be set as a multitude of fractional or integral numbers of International Units. Typically, the operable control member will have a max dose limit block up to a max dose limit (such as up to 60, 80 or 100 units) wherein a further increase in dose size is being prevented by a blocking mechanism incorporated in the drive mechanism of the injection device 100.

In the depicted form, the dose dial scale 170 is provided as a helical type dose dial scale which is so mounted that it moves axially as it is rotated relative to housing 101. FIG. 1 further reveals an axle component which is rotatably mounted but axially fixed relative to housing 101, the axle component functions as a dose setting member 160 which is rotationally coupled with dose dial scale 170 so that these components rotate together but wherein relative axial movements are allowed. During dose setting, a transmission 165 rotationally couples movement of the flexible band 150 with rotation of dose dial scale 170. Hence, each single dose indicia on dose dial scale 170 may be aligned with the scale window of the housing 101 in accordance with the dose set by means of the flexible band 150. The set dose is injected by manually pressing in the injection button 140. During dose injection the dose dial scale 170 returns to its zero position while the transmission 165 couples free the flexible band 150 relative to the dose setting member 160.

The drive mechanism is so configured that when the injection button 140 is in its activation position, e.g. a pushed-in position, the rotation of the dose setting member 160 is coupled with the forward movement of the piston towards the outlet portion 115 of cartridge. The drive mechanism may incorporate a piston rod (not shown) for cooperating with the piston where the piston rod is driven by means of a transmission that only transfers movements of the dose setting member 160 to the piston rod when the injection button 140 is in the pushed-in position. The operation of the drive mechanism of the injection device 100 will not be discussed further in detail herein but may incorporate any suitable mechanism being able to drive the piston of cartridge 110 towards the outlet portion 115 of cartridge 110.

In FIG. 1 is further shown a dose limiter module 200 that in the depicted view is detached from the injection device 100 but which is adapted to be replaceably fitted relative to the injection device 100 by means of a coupling mechanism. In the shown embodiment the dose limiter module 200 is formed to be received in an opening formed in the distal end face of housing 101 so that when the dose limiter module 200 is coupled with the injection device 100, the dose limiter module is accommodated within the housing 101 of injection device 100. In the shown embodiment, the dose limiter module 200 is inserted relative to the injection device along a coupling axis which is parallel to the longitudinal axis of the cartridge. Hence in such configuration the dose limiter module is placed alongside a needle mount (not shown) of the injection device 100.

The injection device 100 may include a latch mechanism (not shown) which is adapted for locking the dose limiter module 200 in place once it has been fully inserted into the injection device. The latch mechanism may be configured so that the dose limiter module snaps in place upon insertion of dose limiter module 200 into housing 101 and configured so that when a release button 180 formed at the distal end of housing 101 of injection device 100 is operated, the dose limiter module 200 is coupled free from the injection device 100. Hereafter, the module may be fitted onto a different injection device. Hence, the dose limiter module 200 may be configured to be used either with a series of consecutive disposable devices, i.e. prefilled devices, or, alternatively, be used with a durable injection device, i.e. a device wherein the cartridge of the injection device is to be replaced by a new one after the contents of the cartridge has been expelled.

In other embodiments of the dose limiter module 200 and the injection device 100, the coupling mechanism may include mutually cooperating coupling means different than the latch mechanism indicated above, for example where the dose limiter module 200 incorporates a latch mechanism internally in a dose limiter base 201 (referred to below).

The coupling mechanism referred to above may incorporate a mechanism that prevents the coupling and the uncoupling of a dose limiter module 200 unless the dose setting member 160 assumes it's zero dose position.

FIG. 2 shows a first embodiment of a dose limiter module 200 in accordance with the invention and also schematically shows a dose setting member 160 of an associated injection device 100 adapted to cooperate with the dose limiter module 200. For reasons of clarity, only the dose setting member 160 of the injection device is shown in FIG. 2.

The dose limiter module 200 includes a dose limiter base 201 which in the depicted embodiment is formed by a proximal housing part 201a and a distal housing part 201b. Accommodated inside dose limiter base 201 is a limiter 240 defining a generally cylindrical shape (see also FIG. 7). The position of limiter 240 is adjustable relative to the dose limiter base 201 along a central axis coinciding with the rotational axis defined by the dose setting member 160 when the dose limiter module 200 is coupled with the injection device 100. As will be discussed below, when the dose limiter module 200 is coupled with the injection device 100, the position of the limiter 240 relative to the dose limiter base 201 defines the maximum dose that can be dialed up by rotation of the dose setting member 160 of the injection device 100.

Dose limiter module 200 further comprises an extension member 260 which is adapted to couple to the dose setting member 160 so that the extension member 260 follows rotation of the dose setting member 160. Arranged between the extension member 160 and the limiter 240 is a track follower 250 having geometries for engaging both extension member 260 and limiter 240. In the shown embodiment, the track follower 250 is defined as a nut having internal and external guide track geometries.

FIG. 2 further shows a lock assembly incorporating a clutch member 230 which is rotationally mounted but axially fixed relative to dose limiter base 230 and a lock operating means. In the shown embodiment, the lock operating means is provided as a lock button 210 which is axially movable from an extended position to a depressed position. Lock button 210 is generally adapted for allowing clutch member 230 to rotate when the lock button 210 is depressed but leaves the clutch member 230 rotationally fixed relative to the dose limiter base 201 at all other times. As apparent from FIG. 3a which is a cross sectional view through the lock button 210 along the central axis in the distal direction, the lock button comprises four axial extensions 211 which render the lock button axially displaceable but rotationally fixed relative to the dose limiter base 201. Further, as seen in FIG. 3b showing a cross sectional proximal view through the assembly formed by clutch 230 and lock button 210, a series of teeth 232 formed in clutch 230 engages corresponding teeth 212 formed in the extensions 211 of lock button 210.

In the state shown in FIG. 2, when the lock button 210 is in its extended position, the engagement between teeth 232 of clutch 230 and teeth 212 of the lock button 210 renders the clutch non-rotatable relative to the dose limiter base 201. However, in the state where the lock button 210 is depressed (not shown), the teeth 212 are pushed out of engagement with the teeth 232 of the clutch, whereby the clutch 230 is allowed to rotate relative to the dose limiter base 201. The dose limiter module 200 further includes a not shown biasing member, such as a spring member, which urges the lock button into is extended position. Also, between clutch 230 and dose limiter base 201, a torsion spring 220 is arranged for urging a torsional force on clutch member, the function of which will be described later.

Figure 4:
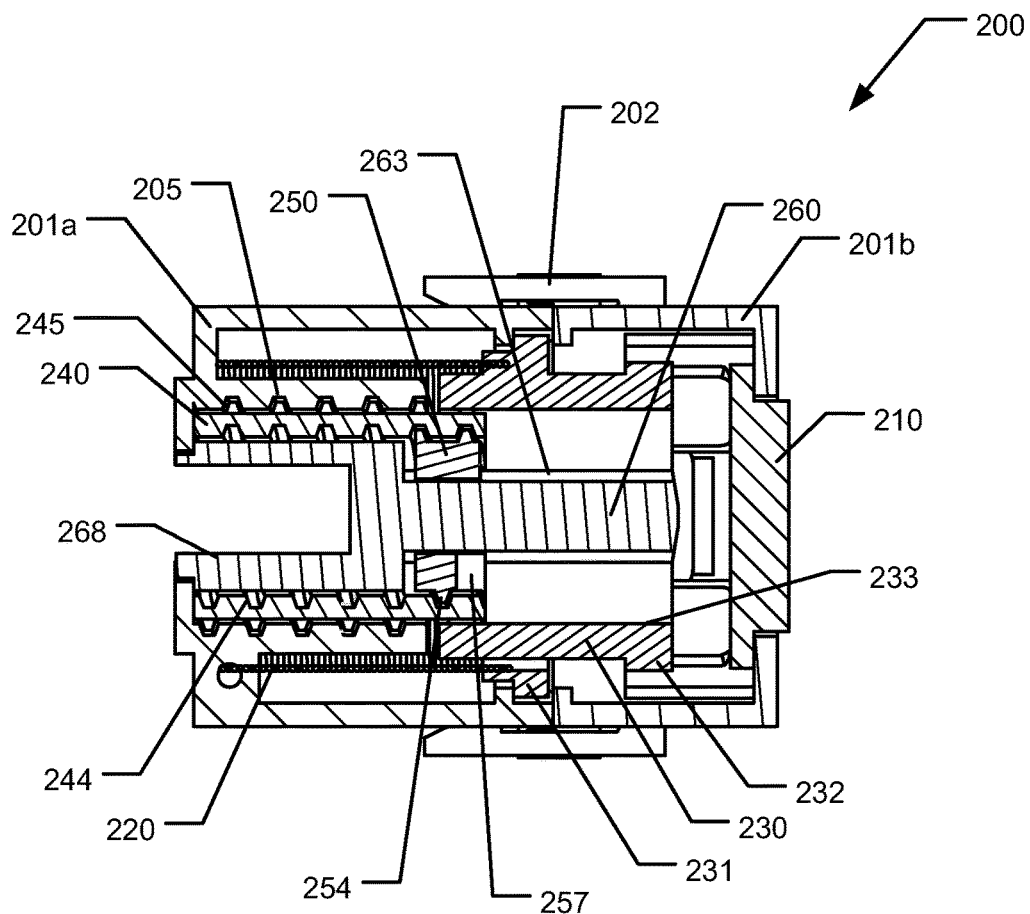
FIG. 4 shows a detailed cross sectional side view of the dose limiter module shown in FIG. 2, incorporating an adjustable limiter and a user operable lock.
Figure 7:
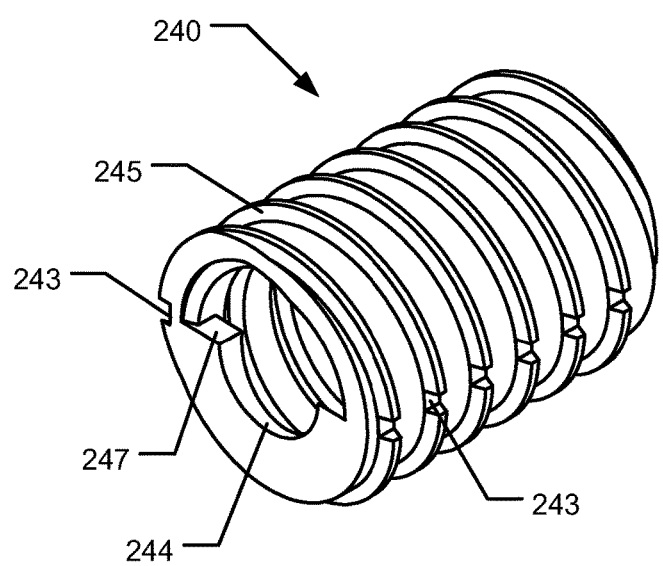

FIG. 4 shows the dose limiter module 200 in a detailed view corresponding to the view shown in FIG. 2. The dose limiter base 201 includes coupling means 202 adapted to cooperate with the latch mechanism of the injection device 100 as referred to above. Also, the dose limiter base 201 defines an internal thread 205 which is configured for engagement with an external thread 245 formed on an outer surface on limiter 240 (see also FIG. 7). Hence, limiter 240 is adapted to move axially relative to dose limiter base 201 when limiter 240 is rotated around its central axis. As seen in FIG. 7, limiter 240 also incorporates two axial tracks 243 each of which is adapted to engage a corresponding geometry e.g. a longitudinal rib 233, formed on the internal surface of clutch 230. Hence, limiter 240 is only allowed to rotate corresponding to the rotation that the clutch experiences when the lock button 210 is in its depressed position. As apparent from FIG. 4 and FIG. 7, limiter 240 further includes an internal thread 244 configured for engagement with an external thread 254 formed on track follower 250.

In the shown embodiment, the pitch of the threaded engagement 205/245 is identical to pitch of the threaded engagement 244/254. However, in other embodiments the pitches of the said threaded engagements need not be the same.

Figure 8:
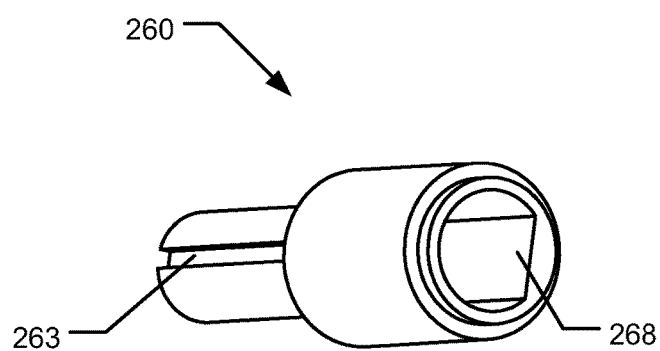

FIG. 4 and FIG. 8 further show the extension member 260 having a proximally facing opening adapted for encircling the dose setting member 160 of the injection device 100, when the dose limiter module 200 is coupled to the injection device. A geometry in the form of a flattened surface 268 is adapted to cooperate with a corresponding flattened surface 168 formed in dose setting member 160 so that the extension member 260 rotates together with the dose setting member 160 during operation of the injection device 100. A distal section of extension member 260 includes a longitudinal recessed track 263 formed in a generally cylindrical outer surface. The longitudinal recessed track 263 is adapted to cooperate with the above mentioned guide track geometry 253 formed on a radially inward facing surface of the track follower 250. Hence, the track follower is configured to follow the rotation of the dose setting member 160 and the extension member 260. In other configurations, the dose setting member 160 and the extension member 260 may be formed as a unitary component whereby the track follower 250 and the dose setting member 160 is formed to ensure that these two components rotate together when the dose limiter module 200 is coupled to the injection device 100 and to enable the track follower 250 and the dose setting member 160 to be separated when the dose limiter module is decoupled from the injection device.

Figure 6:
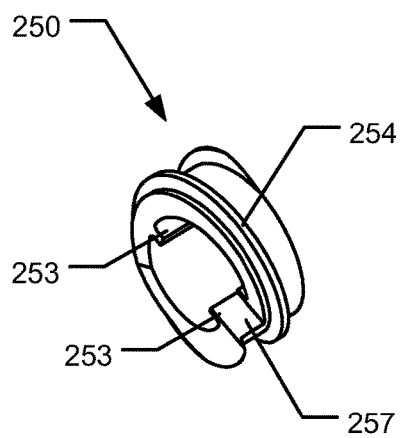

As noted above, the track follower 250 has geometries for engaging both extension member 260 and limiter 240, see FIGS. 4 and 6. Referring to FIG. 6, In the shown embodiment, the track follower includes a linear guide 253 formed on a radially inwards facing surface to cooperate with extension member 260 and an outer helical thread 254 to engage the internal helical thread 244 formed in the limiter 240. The track follower 250 further defines one blocking surface 257 to cooperate with a corresponding counter blocking surface 247 defined by limiter 240 so that the rotational movement of the track follower 250 relative to the limiter 240 is configured to be blocked for a particular relative rotational and axial position between these two components. Hence, provided that the adjusted dose limiting position defined by the limiter 240 is greater than its zero limitation position and the blocking surface 247 does not abut the counter blocking surface 257, the track follower 250 generally moves in the distal direction when a dose is being dialed up and the track follower 250 generally moves in the proximal direction when a dose is being dialed down but also during dose injection.

Figure 5A:
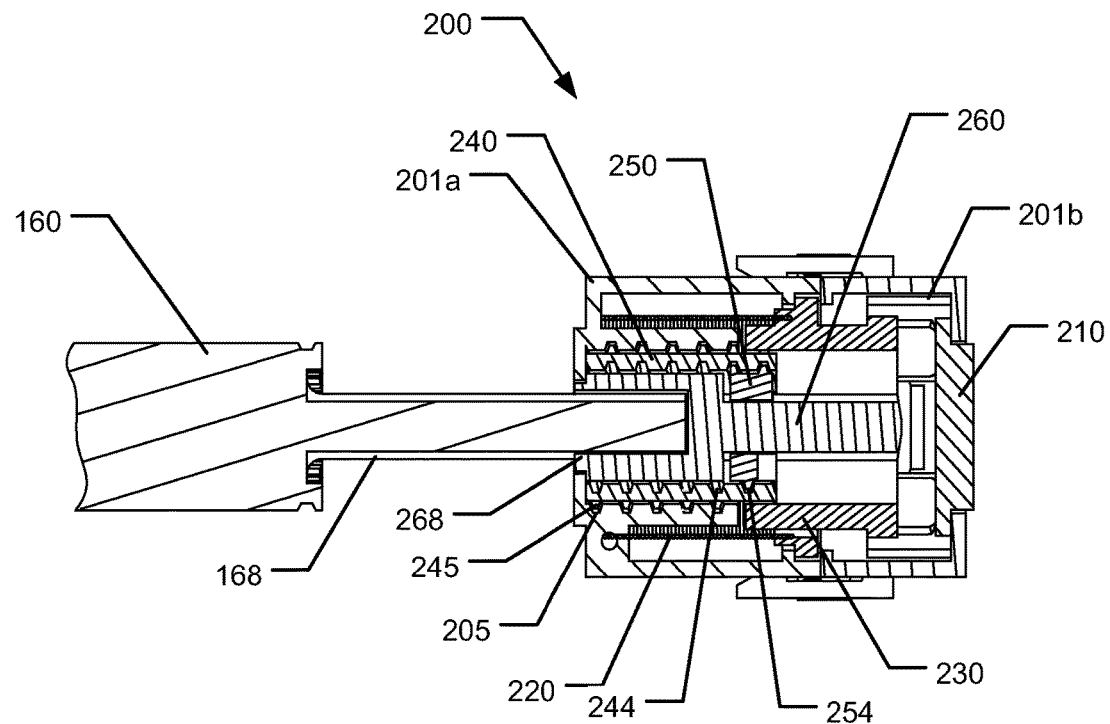
FIG. 5a shows a cross sectional side view of the dose limiter module of FIG. 2 wherein the limiter is positioned in the minimum dose limiting position.
Figure 5B:
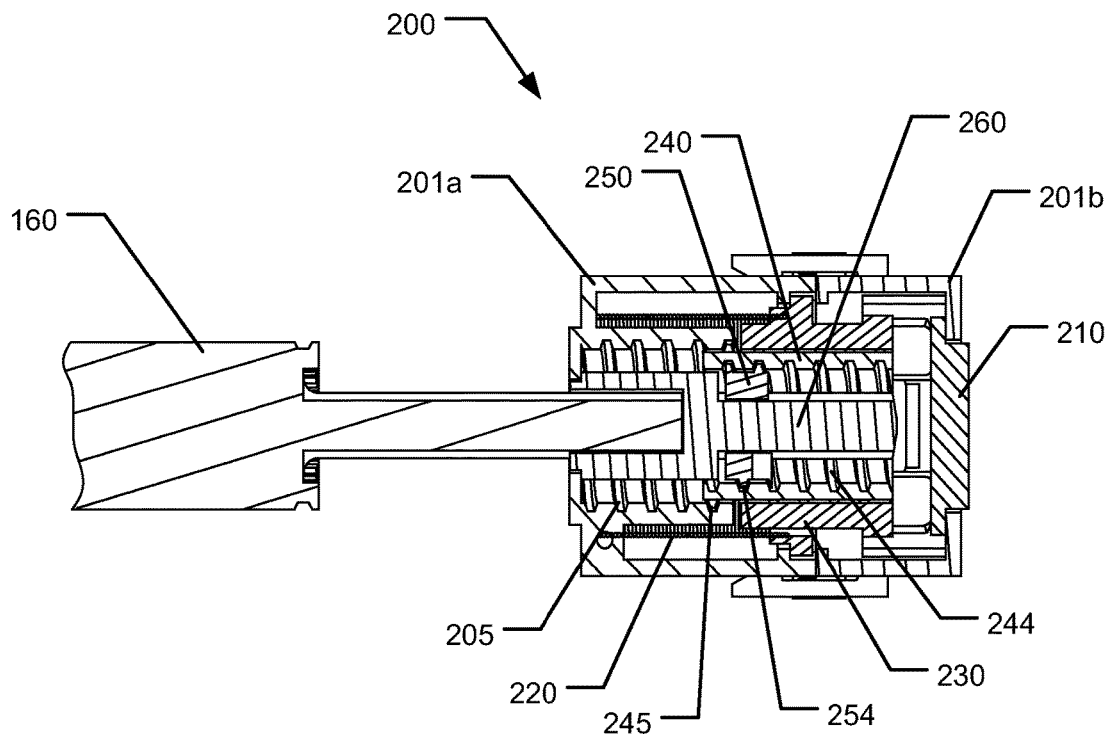
FIG. 5b shows a cross sectional side view of the dose limiter module of FIG. 2 wherein the limiter is positioned in the maximum dose limiting position, and FIG. 6, FIG. 7 and FIG. 8 respectively show perspective views of the track follower, the limiter and the extension member of the dose limiter module according to the embodiment shown in FIG. 2.

Turning now to FIGS. 5a and 5b, these figures again show the dose limiter module 200 and the dose setting member 160 in the coupled configuration, i.e. where the dose limiter module 200 is coupled and latched relative to the injection device 100. In FIG. 5a, the limiter 240 is situated in its most proximal position relative to the dose limiter base 201 while the dose setting member 160 of the injection device 100 has been set to its zero dose size. The track follower 250 assumes a position relative to the dose limiter base 201 in accordance herewith.

In FIG. 5b, the limiter 240 is situated in its most distal position relative to the dose limiter base 201. The track follower 250 assumes the same position relative to the dose limiter base 201 as that shown in FIG. 5a meaning that the dose setting member 160 of the injection device 100 has been set to its zero size.

As will be explained below, the state shown in FIG. 5a depicts the limiter 240 in its minimum dose limiting position whereas the state shown in FIG. 5b depicts the limiter 240 in its maximum dose limiting position.

In the minimum dose limiting position shown in FIG. 5a, where the dose setting member 160 is positioned so that the dose dial scale 170 assumes its zero dosage indication, attempting to rotate the dose setting member 160 for dialing up a dose is prevented due to the blocking surface 257 of the track follower being in abutment with the counter blocking surface 247 of the limiter 240 and due to the limiter 240 being prevented from rotating due to the lock button 210 assuming its locked state.

Upon depression of the lock button 210, while simultaneous operating the dose setting member 160 for dialing up a dose, the limiter 240 starts rotating counter to the force exerted by the torsion spring 220 and in accordance with the thread defined by thread sections 205 and 245 so that the limiter 240 moves axially in the distal direction. The rotation of the dose setting member 160 may be continued until the limiter 240 assumes its maximum dose limitation position shown in FIG. 5b. The dose limiter module 200 may be so configured that this maximum dose limiting position corresponds to the maximum dosage that may be selected by the injection device 100 when no dose limiter module 200 is attached to the injection device. In other embodiments, the maximum dose limiting position may be designed to be below or above the maximum dosage limitation defined by the dose setting mechanism of the injection device.

If the dose limitation module 200 is so adjusted that the limiter 240 assumes its maximum dose limitation position shown in FIG. 5b and the lock button 210 is released, the dose setting member 160 may be operated within the limits defined by the zero dose position (defined by the injection device 100) and the maximum dose limitation position defined by the dose limiter module 200. Hence, from the state shown in FIG. 5b showing the dose setting member 160 where a zero dose has been set on the injection device 100, during dialing up a dose by means of rotating the dose setting member 160, the track follower 250 is moved in the distal direction. During dialing down an initially set dose but also during dose injection, the track follower 250 is moved in the proximal direction.

Between the states shown in FIGS. 5a and 5b, the limiter 240 may be adjusted to assume a particular desired dose limiting position, such as an adjusted dose limiting position corresponding to 12 units, and the lock button 210 is subsequently released to lock the limiter 240 in this particular adjusted dose limiting position. As long as the lock button 210 is in its released position, i.e. the locked state, the dose limiter module 200 determines the maximum selectable dose size that the user will be able to select by operating the dose setting member 160, in this instance limited to a maximum of 12 units. Hence for a particular adjustment of the limiter to correspond to 12 units, the dose setting member 160 may be adjusted to expel dose quantities in the order of 12 units or dose sizes below that size.

Should the user wish to replace the injection device 100, for example if the medicament cartridge contained therein has become exhausted, the dose limiter module 200 may be released from the initial injection device 100 and coupled to a new injection device 100. During this operation, the dose limit adjustment of the dose limiter module 200 will remain adjusted to 12 units so that this adjustment of the dose limiting position is retained when the dose limiter module 200 is coupled to the new injection device 100. Hence, subsequent operation of the new injection device 100 with the dose limiter module 200 attached, the dose setting member 160 may still be adjusted to expel dose quantities in the order of 12 units or dose sizes below that size. Should the user attempt to adjust a dose for sizes above 12 units, rotation of the dose setting member 160 will become blocked by means of the blocking surface 247 abutting the counter blocking surface 257.

As noted above, the torsion spring 220 is arranged between clutch 230 and dose limiter base 201 for exerting a torsional force on clutch member 230. The torsion spring 220 is so configured that upon shifting the lock button 210 into its depressed position, i.e. the unlocked state, the torsion spring 220 acts upon the clutch 230 and thereby also on the limiter 240 so as to urge the limiter 240 towards the minimum dose limiting position. Hence, in order to reduce a once adjusted dose limiting position (say 12 units) the depression of the lock button 210 causes the limiter 240 to move in the proximal direction until the blocking surface 247 and the counter blocking surface 257 abut each other. This will happen when the limiter 240 assumes a position corresponding to the instant dose setting that the dose setting member 160 of the injection device 100 assumes. Ultimately, if a dose size of zero units has been dialed using the dose setting member 160 the limiter 240 moves to its most proximal position relative to the dose limiter base 201, i.e. the minimum dose limiting position.

If the dose limiter module 200 is not coupled to an injection device 100, pressing down the lock button 210 results in the limiter 240 moving in the proximal direction until the limiter 240 assumes its minimum dose limiting position, corresponding to the state shown in FIG. 4. In other embodiments, the dose limiter module 200 may include a mechanism that is so configured that the lock button will only be allowed to enter its depressed position when the dose limiter module is attached to an associated injection device. Hence in such an embodiment, the adjusted dose limiting position cannot be tampered with once the dose limiter module 200 has been detached from an injection device 100.

As noted above, the coupling mechanism between the injection device 100 and the dose limiter module 200 may incorporate a mechanism that prevents the coupling and the uncoupling of a dose limiter module 200 from an injection device 100 unless the dose setting member 160 assumes a particular dose size position, e.g. it's zero dose position. Without such provisions, in situations where the dose setting member 160 is adapted to perform multiple revolutions during dialing up a dose to the max dose setting of the injection device 100, there is a potential risk that the extension member 260 will be mounted in a wrong position relative to the dose setting member 160, causing the track follower 250 to become out of synchronisation with a particular setting of the dose setting member 160 once the dose limiter module 200 is coupled with an injection device 100. Hence, incorporating a mechanism that prevents the coupling and the uncoupling of a dose limiter module 200 from an injection device unless the dose setting member 160 assumes a particular setting can be used to mitigate such issue.

In the embodiment shown in FIGS. 2-8, the track follower 250 includes an internal geometry cooperating with a linear track on the extension member 260, while an outer geometry cooperates with a thread formed in the limiter 240. In other embodiments, the track follower 250 may include an internal geometry cooperating with a thread on the extension member 260, while an outer geometry cooperates with a linear track formed in the limiter 240. In other configurations, the inner and outer geometries may each define threads having different pitches, in a manner similar to the embodiments disclosed in WO 2010/149209. Also, the track follower 250 need not be formed as a nut but may instead be formed as a spherical member as shown in FIGS. 3-8 in WO 2010/149209 or alternatively as a half nut. Also, other geometrical shapes may be used.

In the depicted embodiment shown in FIGS. 2-8, the extension member 260 and the limiter 240 is arranged in a coaxial configuration where the track follower moves in directions parallel to a central axis and where the different parts of the track follower is retained in the same radial distance relative to the central axis as the dose setting member 160 of the injection device 100 is operated.

In an alternative embodiment, a planar configuration may be used instead involving first and second members that are arranged opposite to each other and spaced apart by a particular distance and where the first member and the second member rotates relatively to each other along a central axis when the dose setting member 160 is operated. In such configuration, a track follower may be sandwiched between the first and the second member and be adapted to move along opposing track surfaces formed on the first and second members so that the track follower moves in directions at least partly radially relative to the central axis as the dose setting member 160 is dialed up and dialed down. An adjustable blocking means may then be used for adjusting the maximum dose limit that limits the movement of the dose setting member at a position corresponding to an adjusted dose limiting position.

In still other embodiments, the dose limiter module 200 includes a dose limiter adjustment incorporates a cam and cam follower mechanism where the cam follower is provided by the track follower and adapted to move along the cam track as the dose setting member 160 is dialed up and down during dose setting and as the dose setting member 160 rotates during injection. An adjustable blocking means may be arranged next to the cam track so that the track follower engages the blocking means at a position corresponding to an adjusted dose limiting position.

In a still further embodiment (not shown), the dose limiter module 200 is formed generally corresponding to the dose limiter module 200 as shown in FIGS. 2-8 but where the extension member 260 and the track follower 250 have been omitted. In such an embodiment, the limiter 240 may include a rotational blocking surface arranged at a proximal end of the limiter 240 adapted to cooperate with a corresponding counter blocking surface formed at a distal end the dose dial scale 170 of the injection device 100. Such an embodiment provides a simple alternative to the track follower configuration shown in FIGS. 2-8.

In line with the invention as set forth above, the invention is generally applicable to medical injection devices, regardless of the kind of administration route for delivering a beneficial agent to the user. Also, the invention may be implemented in both injection devices of the non-motorized kind as well as motorized dosers. As regards non-motorized injection devices, such devices both encompass manual injectors where the user directly delivers the necessary mechanical energy during the delivery process as well as spring assisted injectors where a pre-stressed or user strained spring partly or fully delivers the necessary mechanical energy during the delivery process.

In the above description of the exemplary embodiments, the different structures providing the desired relations between the different components just as the means providing the described functionality for the different components have been described to a degree to which the concept of the present invention will be apparent to the skilled reader. The detailed construction and specification for the different structures are considered the object of a normal design procedure performed by the skilled person along the lines set out in the present specification.

The invention claimed is:

1. A medical injection system comprising an injection device and a dose limiter module,
   wherein the injection device is configured for setting and injecting set doses of a drug from a reservoir and comprising a housing and a rotatable dose setting member, and wherein the injection device is configured so that during dose setting, the dose setting member is rotated in a first rotational direction from a first rotational position to a second rotational position in accordance with a size of a dose to be injected, and during dose injection, the dose setting member is rotated counter to said first rotational direction back to said first rotational position,
   wherein the dose limiter module is adapted for being releasably coupled to the injection device to define a coupled state where the dose limiter module is attached to the injection device and to define a decoupled state where the dose limiter module is detached from the injection device, the dose limiter module comprising:
      a dose limiter base,
      a limiter arranged relative to the dose limiter base so that a relative position between the limiter and the dose limiter base is adjustable to set an adjusted dose limiting position of the drug from the reservoir,
   wherein, in the coupled state, the limiter cooperates with the dose setting member to define a blocking structure for preventing rotation of the dose setting member beyond the adjusted dose limiting position when the dose setting member is rotated in the first rotational direction, and
   wherein the dose limiter module comprises a user operable lock configured for operation between a locked state and an unlocked state to respectively prevent and enable adjustment of the position of the limiter relative to the dose limiter base, the lock being configured for maintaining the lock in the locked state at least when the dose limiter module is in the decoupled state.

2. The medical injection system as defined in claim 1, wherein the lock is so configured that, when the dose limiter module is in the coupled state, the lock is shiftable into an unlocked state of the lock to enable adjustment of the position of the limiter relative to the dose limiter base.

3. The medical injection system as defined in claim 1, wherein the lock comprises a lock operating structure that upon user operation shifts the lock from the locked state to the unlocked state to enable movement of the limiter relative to dose limiter base.

4. The medical injection system as defined in claim 1, wherein the limiter comprises a first thread that engages a thread associated with the dose limiter base and wherein a position of the limiter relative to the dose limiter base is adjusted by relative rotation between the limiter and the dose limiter base.

5. The medical injection system as defined in claim 1, wherein the dose limiter module is so configured that when the dose limiter module is in the coupled state, a position of the limiter relative to the dose limiter base is adjustable by structure of the dose setting member of the injection device.

6. The medical injection system as defined in claim 1, wherein the limiter and the dose limiter base are so configured that the limiter is movable between a minimum dose limiting position and a maximum dose limiting position and wherein the dose limiter module further comprises a spring adapted to act upon the limiter for urging the limiter towards the minimum dose limiting position so that when the limiter is positioned away from the minimum dose limiting position the limiter moves automatically towards the minimum dose limiting position when the lock is shifted to the unlocked state.

7. The medical injection system as defined in claim 6, wherein when in the coupled state, the limiter moves automatically into abutment with a track follower, when the lock is shifted to the unlocked state.

8. The medical injection system as defined in claim 1, wherein, when the dose limiter module is in the coupled state, the module and the injection device defines:
- a first member that, at least in the locked state, is non-rotatably mounted relative to the dose limiter base, the first member defining a generally cylindrical surface defining a first track surface,
- a second member that rotates around a central axis and that follows rotation of the dose setting member, the second member defining a generally cylindrical surface defining a second track surface, and
- a track follower arranged between the first member and the second member, the track follower defining a first geometry for engaging the first track surface of the first member and a second geometry for engaging the second track surface of the second member, wherein the first track surface is defined as one of a thread or a longitudinal track for engagement with the first geometry of the track follower, and wherein the second track surface is defined as another one of a thread or a longitudinal track for engagement with the second geometry of the track follower so that the track follower moves along the central axis when the dose setting member is rotated, and wherein the limiter forms a part of said blocking structure for blocking rotation of the dose setting member in the first rotational direction by blocking axial movement of the track follower in accordance with the adjusted dose limiting position of the limiter relative to the dose limiter base.

9. The medical injection system as defined in claim 8, wherein the limiter defines said first member.

10. The medical injection system as defined in claim 8, wherein the dose limiter module defines the track follower and the second member so that when the dose limiter module is in the decoupled state, the track follower and the second member forms part of the dose limiter module.

11. The medical injection system as defined in claim 1, wherein, when the dose limiter module is in the coupled state, the module and the injection device defines:
- a first member that, at least in the locked state, is non-rotatably mounted relative to the dose limiter base the first member defining a cylindrical surface defining a first thread
- a second member that rotates around a central axis and that follows rotation of the dose setting member, the second member defining a cylindrical surface having a second thread, and
- a track follower arranged between the first member and the second member, the track follower defining a first geometry for engaging the first thread of the first member and a second geometry for engaging the second thread of the second member, wherein a pitch of the first thread is different to a pitch of a second thread so that the track follower rotates around the central axis and moves along the central axis when the dose setting member is rotated, and wherein the limiter forms a part of said blocking structure for blocking rotation of the dose setting member in the first rotational direction by blocking axial movement of the track follower in accordance with the adjusted dose limiting position of the limiter relative to the dose limiter base.

12. The medical injection system as defined in claim 1, wherein the injection device includes a rotational dose element that defines a helical thread engaging a helical thread associated with the housing of the injection device, the rotational dose element being adapted to rotate with the dose setting member and wherein the limiter of the dose limiter module, when the dose limiter module is in the coupled state, is adapted to engage said rotational dose element for preventing rotation of the dose setting member beyond the adjusted dose limiting position when the dose setting member is rotated in the first rotational direction.

13. The medical injection system as defined in claim 12, wherein a dose dial scale defines said rotational dose element.

14. The medical injection system as defined in claim 12, wherein the rotational dose element defines one or more rotational blocking surfaces and wherein the limiter defines corresponding one or more rotational counter blocking surfaces and wherein the one or more rotational blocking surfaces engage respective ones of the one or more counter blocking surfaces for preventing rotation of the dose setting member beyond the adjusted dose limiting position when the dose setting member is rotated in the first rotational direction.

15. The medical injection system as defined in claim 1, wherein the limiter and the dose limiter base are adapted for relative rotation over an angle exceeding 360 degrees.

\* \* \* \* \*